United States Patent [19]

Bernardi

[11] Patent Number: 4,891,833
[45] Date of Patent: Jan. 2, 1990

[54] BLINDER FOR CAT SCANNER

[75] Inventor: Richard T. Bernardi, Lincolnshire, Ill.

[73] Assignee: Bio-Imaging Research, Inc., Lincolnshire, Ill.

[21] Appl. No.: 296,412

[22] Filed: Jan. 9, 1989

Related U.S. Application Data

[63] Continuation-in-part of Ser. No. 122,905, Nov. 19, 1987, abandoned.

[51] Int. Cl.$^4$ .............................................. G21K 1/04
[52] U.S. Cl. ................................... 378/145; 378/146; 378/151; 378/152
[58] Field of Search .................... 378/8, 19, 145–147, 378/95, 150, 151, 152, 205

[56] References Cited

U.S. PATENT DOCUMENTS 3,588,511  6/1971  Montagne ........................... 378/152
4,005,311  1/1977  Ledley ................................... 378/8

Primary Examiner—Carolyn E. Fields
Assistant Examiner—David P. Porta
Attorney, Agent, or Firm—Laff, Whitesel, Conte & Saret

[57] ABSTRACT

A dynamic scanning X-ray machine has a detector with an array of crystals which respond to X-rays and a circuit made of semiconductor material, both of which deteriorate when exposed to X-rays. A pair of blinder plates which are opaque to X-rays normally cover the detector and semiconductor material to prevent their deterioration by the X-rays. The blinder plates are separated from each other by an adjustable distance to form a gap which enables the X-rays to reach the detector. An object under study and the blinders move in synchronism through the X-ray field so that a part of the X-ray field forming the shadow of the object passes through the gap formed by the separation between the blinder plates and falls upon the detector, while the detector crystals and semiconductor material are shielded from the remainder of the X-ray field. The shielding of the detector crystals and semiconductor material does not have any effect upon the image of the object under study. The distribution of a field of light simulates the distribution of the field of X-rays. The light is reflected by mirrors onto a photocell sensor which can thus detect the presence of X-rays without being exposed to them.

17 Claims, 5 Drawing Sheets

FIG. 4
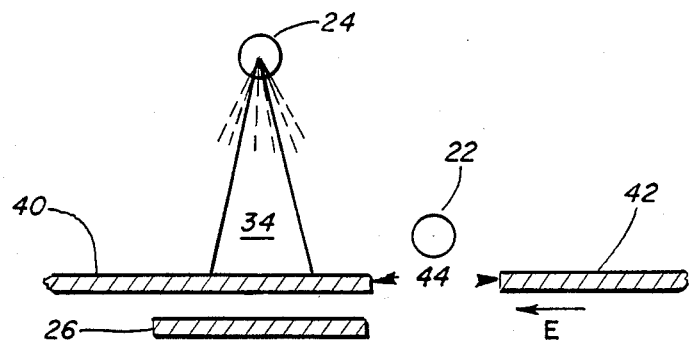
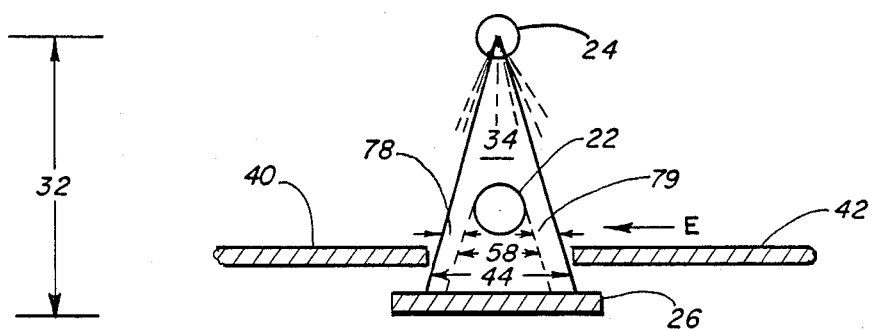
FIG. 5
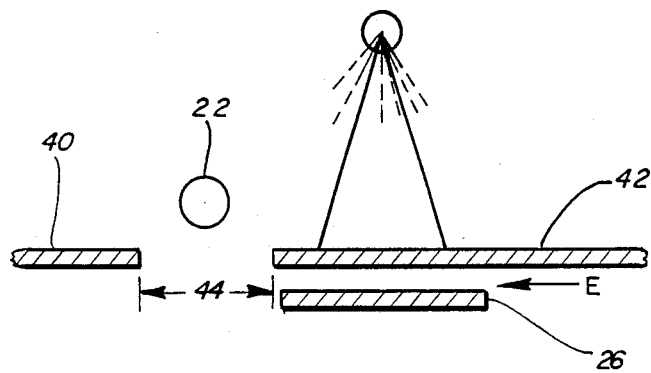
FIG. 6

BLINDER FEEDBACK CONTROL CIRCUIT

BLINDER FOR CAT SCANNER

This application is a continuation-in-part of application Ser. No. 122,905, filed Nov. 19, 1987, now abandoned.

This invention relates to computed tomography ("CAT or CT scanners") and more particularly to means for and methods of prolonging the life of solid state detectors used therein.

Reference is made to my simultaneously filed and copending patent applications (Ser. No. 122,797), entitled "Automatic Dynamic Focusing For Computed Tomography" and (Ser. No. 122,909), entitled "Cam-Controlled Automatic Dynamic Focusing For Computed Tomography" for a further description of some of the elements disclosed herein.

Industrial computed tomography scanners ("CAT scanners") can have high energy X-ray sources which utilize solid-state X-ray detectors that may be damaged when exposed over a long term to high energy radiation. For example, radiation-sensitive components of such solid-state X-ray detectors may include such elements as inorganic scintillation crystals, silicon photodiodes, and general electronic components such as operational amplifiers.

Among what are known as second generation CT scanners, the position of the scanned object is translated or linearly moved relative to the X-ray beam. The second generation systems require the entire beam to both precede and follow the scanned object during its translation or movement; i.e., the illuminated area is much larger than that required to scan the X-rayed object. During the time that the scanned object is in the path of the X-ray beam, its shadow attenuates and reduces the radiation falling upon the detectors used for collecting data. However, during the time that the translating beam precedes and follows the moving object, the detectors are exposed to an unattenuated X-ray beam. Thus, the greatest damage to the detectors occurs during this latter period.

For previously developed medical CAT scanners, X-ray sources have had low potentials such as 150 KV, and consequently radiation damage was of little concern. However, in order to further improve the x-ray penetrating capability of CAT scanners, especially industrial CAT scanners, it is desirable to use a 2 MV linear accelerator x-ray source. At the resulting high energy levels, the detector life may be reduced significantly, due to radiation damage. Moreover the expense of replacement of radiation-damaged, solid-state X-ray detectors is prohibitive. As the energy levels of the X-ray sources go still higher (e.g. 16 MV), this problem of radiation damage becomes more severe.

According to this invention, the solution to the problem of X-ray caused damage to solid-state devices involves the use of smart, dynamic blinders (radiation attenuators) associated with the leading and trailing edges of an unattenuated X-ray beam. The blinders are devices which are designed to absorb X-rays and to minimize the time that a detector is exposed to maximum radiation. As a result, the useful life-span of a solid-state X-ray detector can be increased.

Accordingly, an object of the invention is to provide new and improved X-ray machines having extremely high levels of radiation, and to shield electronic equipment (especially semiconductor material) from high-energy X-rays which damage the equipment. In this connection, an object is to expose X-ray detector crystals to damaging X-rays during only a minimum period of time.

Another object of the invention is to provide dynamic X-ray absorbing blinders which travel with an object under study to expose semiconductor detector crystals to X-rays during only a minimum period of time while the shadow of each object is passing over them.

In keeping with an aspect of the invention, these and other objects are accomplished by providing a pair of lead-filled panels or blinders which may be separated from each other by a minimum distance, thus forming an aperture for passing an X-ray beam. These panels are mounted to move with the object under study so that the blinders cover the detectors during the time periods while the object is approaching a detector, and after it leaves the detector. This way, the detector is exposed only during the very brief period while the shadow of the X-rayed object is actually over the detector. Mounted on the blinders are photosensitive diodes which can respond to a source of light that mimics the X-rays; i.e., if the light is present, the X-rays are also present. These diodes control the movement of the blinders and coordinate their travel with the movement of the object being studied.

A preferred embodiment of the invention is shown in the attached drawings, in which:

FIG. 1 is a perspective view which pictorially shows a CAT scanner incorporating the invention;

FIG. 2 schematically represents the CAT scanner of FIG. 1, seen in a top view;

FIG. 3 schematically represents the same CAT scanner, seen in a side view;

FIG. 4 schematically shows the object under study approaching a detector;

FIG. 5 schematically shows the object under study over the detector, with the entire shadow of the object on the detector;

FIG. 6 schematically shows the object under study after it has left the detector;

Figure 1:
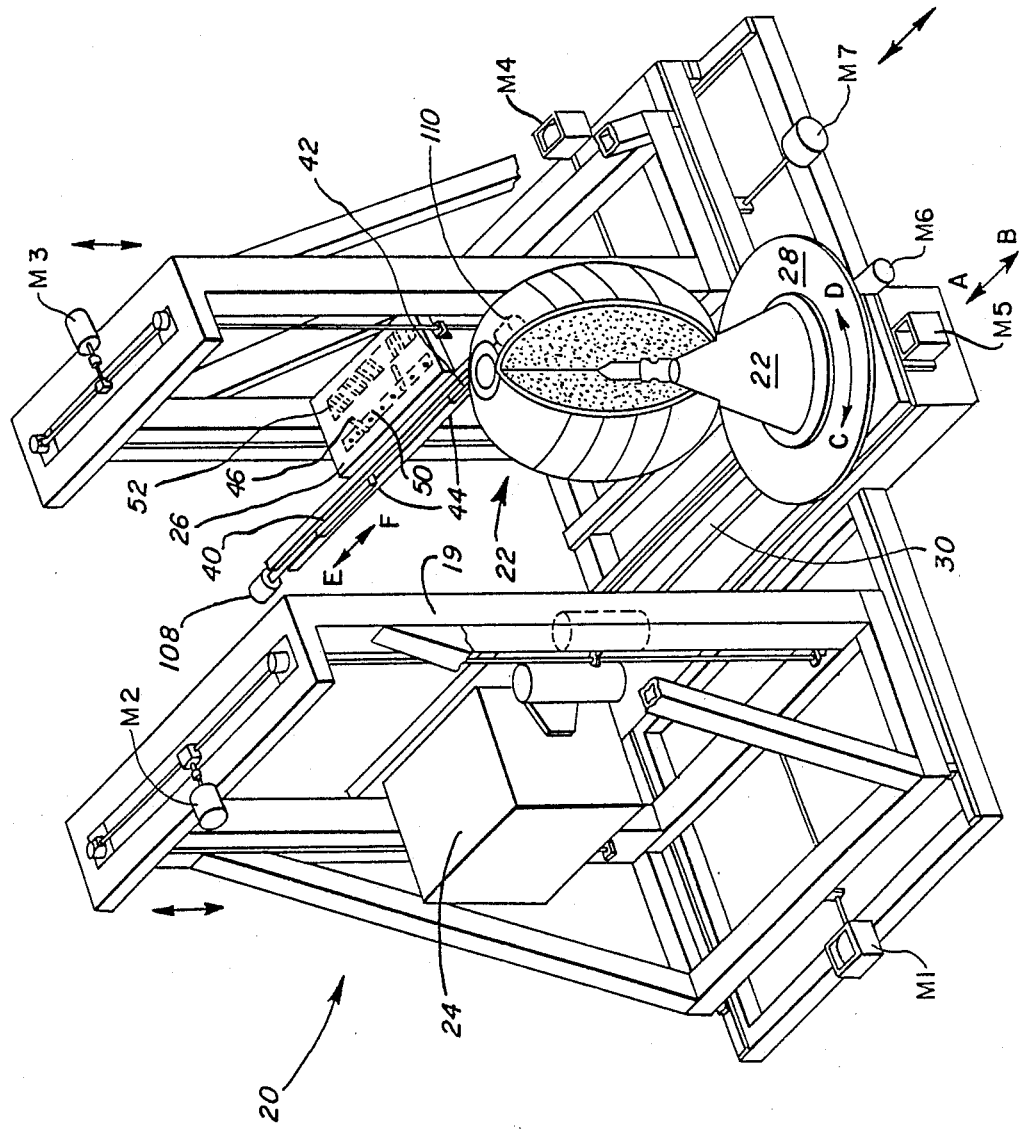

FIG. 1 pictorially indicates the inventive CAT scanner 20 as it is being used to X-ray an object 22 under study, which is here shown, by way of example, as a rocket motor. A frame 19 supports a source 24 of X-rays, such as a 150 KV or 420 KV tube, or a 2 MV linear accelerator, and an opposed X-ray detector 26. The frame enables the X-ray sources and the detector to move to any suitable points in a spaced parallel pair of vertical planes. The 2 MV X-ray source 24 illuminates the detector 26 and will damage or destroy it prematurely, unless some protection is provided.

The object 22 under test is mounted on a turntable 28 which rotates as the object 22 is being X-rayed. The turntable 28 is mounted on a carriage which travels in directions A,B over track 30. Thus, the object 22 exposes all of its surfaces to X-rays as it travels with both linear and rotary motion through the space between the source 24 and the detector 26.

A computer responds to the resulting signals from the detector 26 to constuct a tomographic X-ray image of object 22. A number of separate motors M1-M4 drive the supporting frame structure to position the X-ray source 24 and the detector 26 relative to the object 22 under study. A motor M5 operates a translational drive which moves the object 22 under study linearly (directions A,B). Motor M6 moves the object rotationally (directions C,D).

Figure 2:
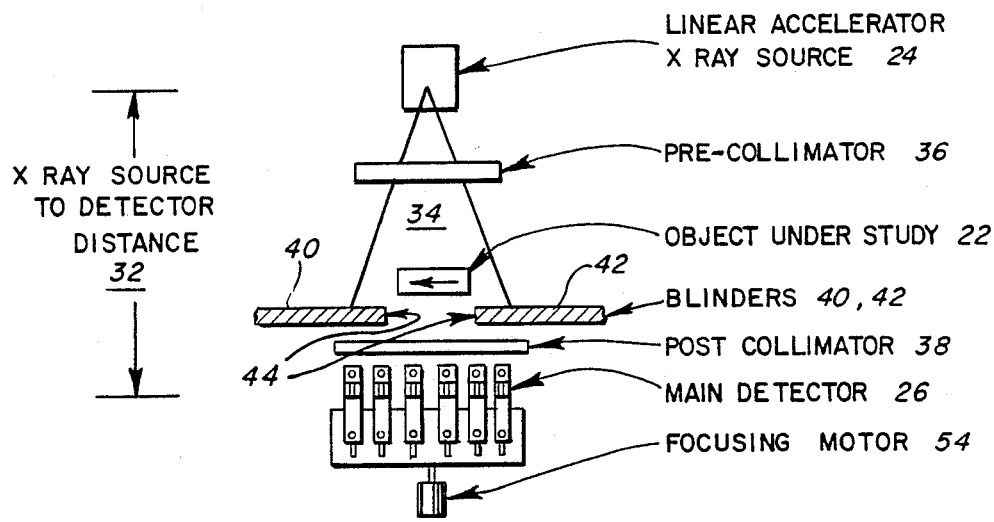
Figure 3:
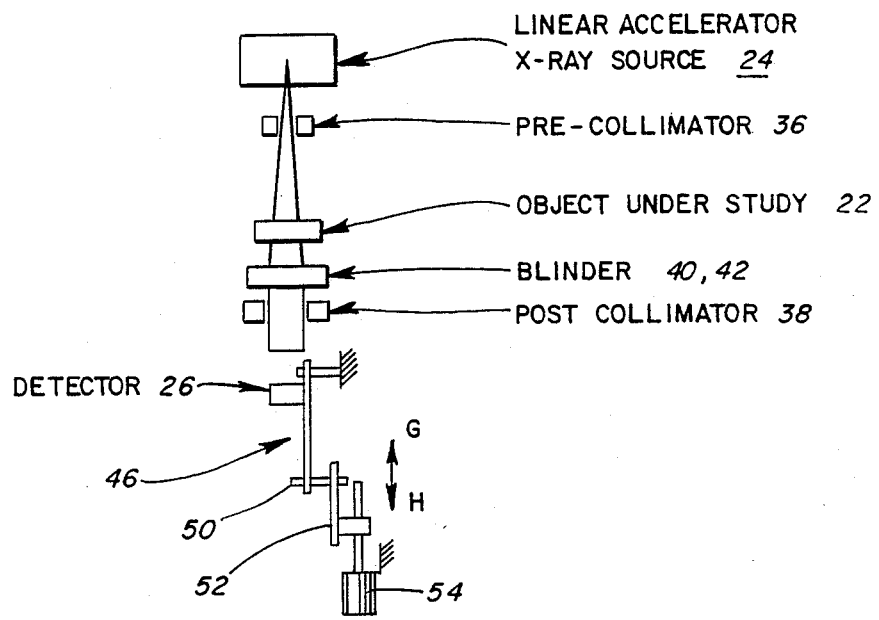

The operation of the CAT scanner of FIG. 1 is explained with the help of schematic FIG. 2 which is a top view and FIG. 3 which is a side view of the structure shown in FIG. 1. The source 24 of X-rays is displaced from a detector 26 by a source-to-detector distance ("SID") 32 which may vary. The X-rays tend to spread into a somewhat fan-shaped pattern, as seen at 34. Precollimator and post-collimator beam shapers 36, 38 are positioned within the path of X-rays to control and reduce the width or thickness of this fan-shaped pattern of X-rays. A pair of plates 40, 42 made from material (such as lead) which is opaque to X-rays forms a pair of blinders which define between them the length of slot 44 through which X-rays may pass in order to illuminate the surface of detector 26, without an unnecessarily prolonged exposure to X-rays.

The object 22 under study moves past the blinders 40, 42 and across the exposure slot 44 where it casts a shadow in the X-rays illuminating the scintillating surface of crystals forming detector 26. The crystals of the detector 26 give an image signal in the outline and form of the object under study, which is the desired X-ray image.

From an inspection of FIGS. 2 and 3, it appears that as the X-ray source-to-detector distance 32 increases or decreases the fan-shaped X-ray beam spreads or contracts, thereby changing the degree of magnification and the angle of incidence upon the illuminated surface of the detector 26. Therefore, the width of the exposure slot 44 may be adjustable by moving the blinders 40, 42 together or apart.

The detector 26 crystals are packaged in a plurality of elongated strips 46 (FIG. 3) which are pivotally connected at one end 48 to the machine and at the other end 50 to a cam-follower which rides in an individually associated cam slot formed in a focuser plate 52. As a focusing motor 54 drives the focuser plate 52 back and forth in directions G,H, the cam contolled end 50 of the strip 46 of detector crystals swings into a position where an optimum image is formed.

Two "smart" blinders 40, 42 are shown in FIGS. 1, 2 and 4-6. Preferably, the blinder is designed to attenuate a 2 MeV linear accelerator with an X-ray beam output of 200 rads per minute, at a distance of one meter, in air. At a distance from the source which is greater than two meters in air the blinder is more than sufficient to attenuate the X-rays when the blinder material is equivalent to at least a two-inch path through lead or any other suitable material of equal or greater density.

In greater detail, the blinders 40, 42 are fabricated from a dense high-Z (atomic number) material such as lead or tantalum, which attenuates over 90% of the X-ray beam. The attenuation occurs where the X-rays are not used for collecting CAT scan data. For proper shielding, each blinder must be wider than the largest X-ray beam slot or the widest beam slice, and longer than the length of the linear X-ray detectors 46. Each blinder 40, 42 shields the detector 26 and moves as a function of the leading and trailing edge positions of the object under study. Therefore, a closed-loop position feedback control circuit may maintain proper spacing between the blinders for attenuating the X-rays during the CAT scan.

The blinders 40, 42 (FIG. 5) are moved a pre-selected distance to form a slot length 44 that is slightly wider than the shadow 58 cast by the object under study. It should be apparent that, if the SID distance 32 between the source 24 and the detector 26 is increased, the beam spot or base of the fan-shaped conical X-ray pattern 34, representing the spread of the X-rays, becomes larger. Thus, the distance across the slot 44 must then be adjusted so that it also becomes larger. Conversely, if the distance 32 becomes less, the beam spot or base of the conical X-ray pattern 34 becomes smaller, and the length of slot 44 is adjusted to become smaller.

In operation (FIG. 4), the object 22 is not yet within the X-ray pattern and is not over the detector 26. Thus, blinder 40 must be wide enough to shield the detector 26 from all X-rays 34. As indicated by the arrow E, the object 20 is moving toward the detector 26, and may also be rotating (direction E could correspond to either direction A or B in FIG. 1). The rotation of a circularly symmetric object such as a rocket motor 22 does not have an effect upon the positioning of either the shadow or the width of the slot gap 44. However, rotation of asymmetric objects would change slot gap 44.

As shown in FIG. 5, both of the blinders 40, 42 and the object 22 have moved in direction E, to a position where both object 22 and slot 44 are over detector 26. At this point, the shadow or image of the object under study passes through slot 44 and is cast upon the detector 26.

Based on anticipated high energy scanner use, and with the use of the above-described dynamic blinders, main detector life increases so much that replacement of the detector is unlikely during the scanner life expectancy. Without the dynamic blinders, main detector replacement would be required many times during the useful scanner lifetime. The cost of incorporating the blinders is estimated to be less than 15% of the cost of a single such replacement.

In FIG. 5, both the blinders 40, 42 and the object 22 are in a position such that the entire shadow 58 is over detector 26 during translation of the object. Within gaps 70 and 71 the x-ray detectors 26 see the full unattenuated x-ray beam near the leading and trailing edges of the shadow 58 of object 22. The blinders minimize gaps 78 and 79 during translation to increase the life of detectors 26.

In FIG. 6, both the object 22 and the gap 44 have passed away from the detector 26. The blinder 42 has moved far enough in direction E to completely shield the detector 26 from the X-rays.

Another problem addressed by the invention is to create and to detect the proper slot length and to control the blinder movement, as taught by FIGS. 4-6. The detector 26 itself could be used as a means for sensing both the proper blinder position and direction of travel provided that the CAT scan system has a central data acquisition system, a central processing system, and an array processor. This approach, however, may interfere with the primary function of collecting CAT scan data by subjecting the data acquisition and processing system to additional demands for real-time processing.

Figure 10:
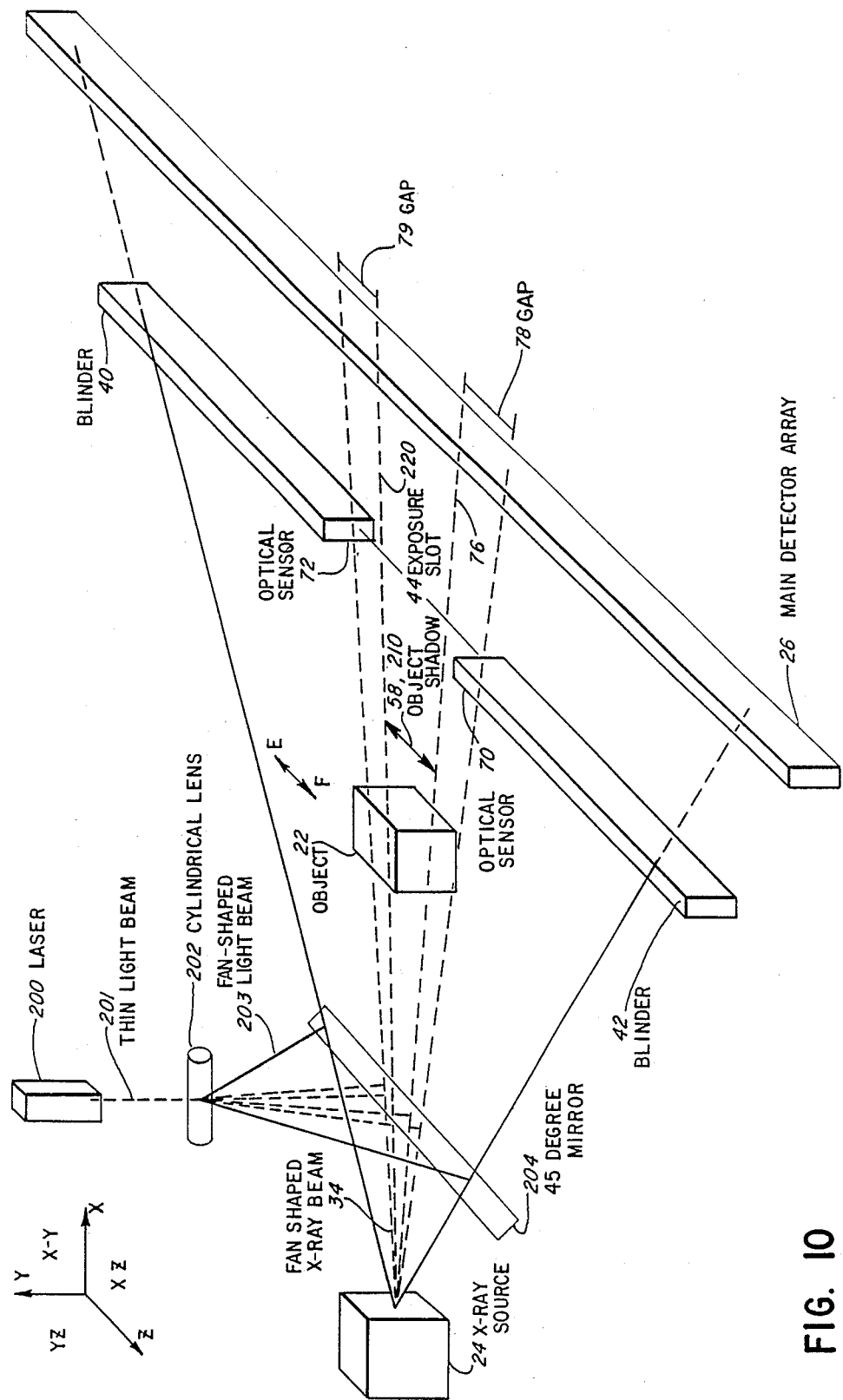
FIG. 10 is a perspective view which schematically shows the creation of a non-X-ray field used to mimic the X-ray field.

A better approach, which is used in the preferred embodiment, is to sense the object's X-ray shadow position and control blinder movement using facilities separate from the CAT scan data acquisition system. This scheme is shown generally in FIG. 10. A set of coordinate axes (x, y, and z), along with matching planes (xy, xz, and yz), are provided for convenient description of the orientation of various items.

A light source 200 creates an optical light field 203 which, after reflection by a 45-degree mirror 204, closely coincides with the X-ray fan beam 34 so that an object 22 travelling through the path of the X-ray beam 34 casts an optical shadow 210 which is nearly identical to its X-ray shadow 58. Blinders 42, 40 form an exposure slot 44 which defines the outer limits of the data collection region. The exposure slot 44 must be somewhat larger than the object shadow 58, 210, thus providing a pair of gaps 78, 79 on either side of the object shadow. These gaps define regions in which the X-ray beam 34 is unattenuated (either by the blinders or the object). The full-strength beam in the gap region is used to calibrate each detector in the detector array 26 during each scan.

Optical sensors 70, 72 on each blinder 42, 40 detect the leading and trailing edges 76, 220 of the object's optical shadow, and from this information, the current blinder positions and direction of travel with respect to the object's shadow can be determined. An independent control system monitors these positions and controls drive motors to dynamically adjust the blinders to optimal locations in response to information received from the sensors.

The light source 200, typically a low-powered helium-neon laser, produces a thin beam of light 201 with an approximately circular cross-section and negligible divergence. In order to accurately mimic the X-ray fan beam 34, the non-divergent light beam 201 must be converted into a fan-shaped beam (that is, a planar beam which diverges in one dimension), and its position must be made to coincide fairly closely with that of the X-ray fan beam.

The light source 200 is mounted above and in front of the X-ray source 24 to produce a light beam pointing downward, perpendicular to the xz plane. A cylindrical lens 202 is interposed in the path of the light beam to cause it to diverge into a fan-shaped beam 203. The cylindrical lens 202 is oriented with its cylindrical symmetry axis perpendicular to the yz plane, so that the resulting plane of the fan-shaped light beam 203 is parallel to the yz plane.

A mirror 204 is placed at a 45-degree angle (i.e. parallel to a plane defined by the equation $x+y=c$) at the intersection of the fan-shaped light beam 203 and the X-ray fan beam 34 to redirect the light beam into the plane of the X-ray beam. Because the mirror 204 is located in the X-ray beam path, it must have low X-ray attenuation to prevent undesired effects on image data collection. The effective optical distance between the cylindrical lens 202 and the object 22 over the reflected light path must be approximately equal to the X-ray-source-to-object distance in order to ensure that the divergence angle of both beams are the same.

The object 22 therefore casts an X-ray shadow 58 and an optical shadow 210 which are essentially coincident, subject to errors introduced by misalignment of the laser 200, cylindrical lens 202, and mirror 204. This alignment is not critical provided that the total error produced thereby is small compared to the size of gaps 78 and 79. Similarly, while the blinder travel speed must be near the actual translation speed of the object shadow 58, precise regulation of the speed is of little importance as long as acceptable gaps 78 and 79 are maintained between the blinder and the object shadow edges and the relevant portion of the X-ray beam so that the image reaches the detector 26.

Figure 7:
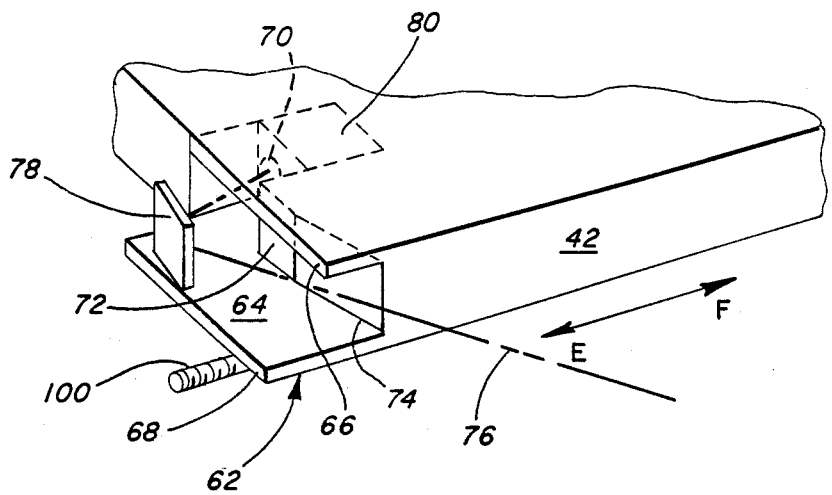
FIG. 7 is a perspective view of a blinder with a leading edge sensor.

FIG. 7 shows the arrangement of the exemplary leading edge sensor 70 of blinder 42. This sensor responds to visible light such as that present in the reflected optical fan beam 203. In order to detect the leading and trailing edges 76, 220 of the object shadow 210, sensor 70 is mounted in the corner of blinder 42 at the edge of the exposure slot 44. The exposure slot 44 is created by the space between the two blinders and defines the outside edges of the data collection region. A similar sensor 72 (shown only in FIG. 10) is mounted in a corresponding location on blinder 40.

As previously mentioned, the exposure slot 44 must be somewhat larger than the object shadow 210 to provide gaps 78, 79 on either side of the shadow. These gaps provide a small region of unattenuated X-ray beam used for main sensor calibration. Also, the gaps act as guard bands to render blinder position and registration of the X-ray and optical fan beams less critical. In order to create such a gap, it would be desirable for sensor 70 to be offset a small predefined distance into the exposure slot 44 so that the sensor could detect the leading edge 76 of the object shadow before the shadow actually reaches the tip of the blinder. The blinder positioning system could then dynamically adjust the blinder position so that sensor 70 tracks the object shadow's leading edge 76 and the edge of the blinder would precede the object shadow by the predefined distance.

Such placement of the sensor 70 within the exposure slot 44 has the disadvantage that the sensor would attenuate the X-ray beam and thus would interfere with the primary function of collecting CAT scan image data. In addition, the optical sensor may deteriorate from continuous exposure to X-rays. Accordingly, optical sensor 70 is buried within a recess formed in a corner of the leading edge of blinder 42. (A similar arrangement is provided for sensor 72 in blinder 40.) An optical mirror 78 reflects light from the optical fan-beam 203 to the sensor 70. The mirror is made from material which is essentially transparent to X-rays. This arrangement of sensor 70 and mirror 78 prevents these components from interfering with the X-ray beam and the acquisition of image data. In addition, because the blinder is made from an X-ray attenuating material such as lead, the recessed optical sensor is protected from X-ray damage.

In greater detail, the corner 62 of the blinder 42 is milled or otherwise hollowed to provide a recess or cavity 64 with overhanging ledges 66, 68, the latter mounting a mirror 78 which is mostly transparent to x-rays. Deep within the recess 64 is sensor 70, which may be any suitable photosensitive device. The preferred sensor is one which is sensitive to red light in a range of the spectrum which may be delivered by a helium neon laser.

The recess 64 is shaped to provide an outstanding wall portion 72, projecting forward of the sensor in order to protect it from radiation. The recess edge 74, which is between the sensor 70 and the X-ray field, is angled to enable the laser beam 76 to be directed onto the reflective face of mirror 78 which reflects it around wall portion 72 and on to the sensor 70. Thus, sensor 70 detects the location of a light field relative to a leading edge of blinder 40 or 42, while being protected from the damaging radiation of the X-rays.

Figure 8:
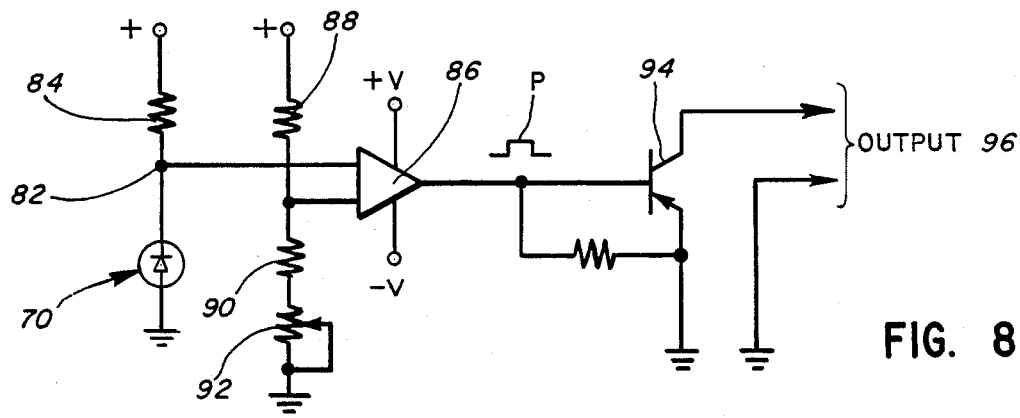
FIG. 8 is a schematic circuit diagram showing a sensor and its associated circuitry used in connection with the blinder of FIG. 7.

A compartment 80 is built into the recess 64 within blinder 42 in order to also protect from radiation damage electronic devices which are associated with the sensor 70. This associated circuit is shown schematically in FIG. 8. When no light is shining upon sensor diode 70, potential point 82 is at the battery potential (+) which is applied through a current-limiting resistor 84. When light is present, sensor diode 70 conducts and potential point 82 goes to ground potential. A differential amplifier 86 has one input which is biased to a reference potential via a voltage divider 88, 90 in accordance with the setting of potentiometer 92.

Thus, the amplifier 86 conducts to give an output signal P only after photo-switch diode 70 conducts to apply ground potential. When the output signal P appears, an electronic switch 94, in the form of a PNP transistor, conducts to give an output signal at terminals 96.

A switchable servo system is provided to control the movement of the blinders 40, 42 in response to the output signal at terminals 96. In greater detail, one or more feed screws 100 (FIG. 7) is threaded through individually associated nuts attached to the bottom of the blinder 42. Thus, if the feed screw 100 is rotated in one direction, blinder 42 is driven in direction E. If turned in an opposite direction, the blinder is driven in direction F. The two blinders 40, 42 may be driven separately. Therefore, an associated computer may calculate the desired width of the slot gap 44 and pre-position the blinders accordingly. Thereafter, the two blinders move as a unit to preserve the pre-set slot width.

Figure 9:
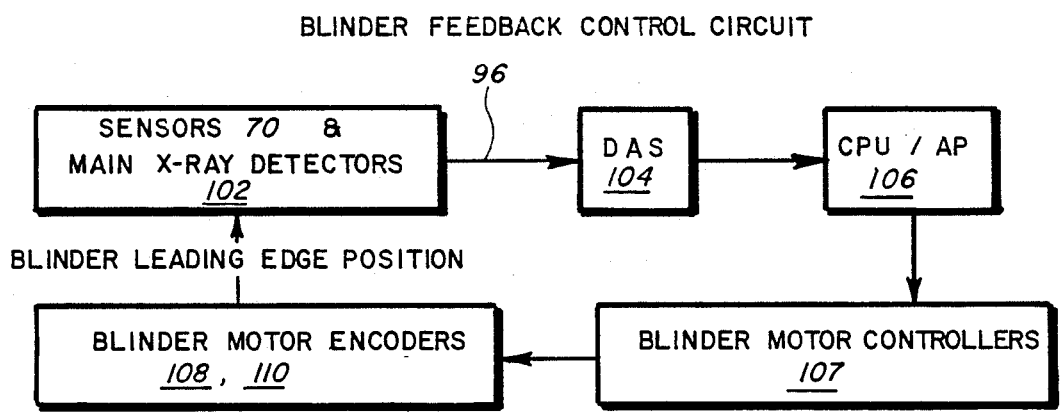
FIG. 9 is a block diagram of a servo system for controlling the movement of the blinders.

The circuit for controlling the blinder position is shown by the block diagram of FIG. 9. More particularly, sensor 70 and the main X-ray detectors 102 comprise the circuit of FIG. 8 which is repeated at as many positions on the blinders 40, 42 as may be appropriate and necessary, to detect the boundary of the X-ray beam spot relative to slot 44. The data resulting from the collective output terminals 96 is fed into a data acquisition system 104 which converts the sensor outputs into any suitable form of signal that is usable by a central processing unit ("CPU") 106. The CPU applies a drive signal to blinder motor controllers 107 which selectively energize blinder control motors 108, 110 (FIG. 1). These motors move the blinders 40, 42 to position their leading edges at the proper gap width 44, and thereafter to move the two blinders as a unit. The blinder travel speed and motion may be controlled by any suitable type of microprocessor 106 for calculating the time, place, and duration of the exposure of the detector 26 to X-rays. A feedback loop from the motors completes a closed servo loop, since the sensors 102 confirm the positioning of the blinders to the CPU.

The blinders 40, 42 travel in synchronism with the shadow of translating object 22, so that the image or shadow of the object 22 passes through the gap 44 and falls on the detector 26 (FIG. 5). The blinders 40, 42 may independently travel either faster or slower than object 22 travels, depending upon the magnification of the distance between the leading and trailing edges of the object image, upon the gap width, and upon the nature of the scan.

The motors (108, 110, FIGS. 1 and 9) for positioning the blinders may be controlled by a commercial servo system available from A.S.R. Servotrol Inc., having an office at 7945 Deering Avenue, Canoga Park, Calif. 91304 (their model TSNM is preferred). The blinder motor controllers 107 (FIG. 9) may be a "Multibus" motor controller, model DMC/200 which is available from Galil Motion Control Inc., 1928-A Old Middlefield Way, Mountain View, Calif. 94043.

Those who are skilled in the art will readily perceive how to modify the invention. Therefore, the appended claims are to be construed to cover all equivalent structures which fall within the scope and spirit of the invention.

I claim:

1. A dynamic X-ray scanner comprising a source of X-rays, a detector means at a location for detecting said X-rays, said detector means comprising a plurality of detector units, said detector units being made of a material which deteriorates on exposure to said X-rays, means for moving an object under study between said source and said detector means so that a shadow of said object falls on at least some of said detector units, blinder means having a gap through which said X-rays must pass in order to fall on said detector means, and means for moving said blinder means in synchronism with the movement of said object under study so that said gap is over each of said detector unit substantially only when an X-ray shadow of said object falls on said detector units.

2. The scanner of claim 1 wherein said object shadow has a width, and said blinder means comprises two plates which are made of a material that is substantially opaque to said X-rays, said two plates being positioned adjacent each other to define said gap between them, and automated means for adjusting the length of the gap between said two plates in response to the width of said object shadow.

3. A dynamic X-ray scanner comprising a source of X-rays, a detector means at a location for detecting said X-rays, said detector means being made of a material which may deteriorate on exposure to said X-rays, means for moving an object under study between said source and said detector means so that a shadow of said object falls on said detector means, blinder means having a gap through which said X-rays must pass in order to fall on said detector means, and means for moving said blinder means in synchronism with the movement of said object under study so that said gap is over said detector means substantially only when an X-ray shadow of said object falls on said detector means
wherein the blinder means attenuates a 2 MeV linear accelerator with an X-ray beam output of 200 rads per minute at one meter in air, and the blinder means attenuates more than 90% of the X-ray beam at a distance from the source which is greater than two meters in air.

4. A dynamic X-ray scanner comprising a source of X-rays, a detector means at a location for detecting said X-rays, said detector means being made of a material which may deteriorate on exposure to said X-rays, means for moving an object under study between said source and said detector means so that a shadow of said object falls on said detector means, blinder means having a gap through which said X-rays must pass in order to fall on said detector means, and means for moving said blinder means in synchronism with the movement of said object under study so that said gap is over said detector means substantially only when an X-ray shadow of said object falls on said detector means
wherein said blinder means inserts a material between said source and said detector means which provides a path having an x-ray attenuation which is equivalent to the attenuation provided by at least a two-inch thickness of lead.

5. A dynamic X-ray scanner comprising a source of X-rays, a detector means at a location for detecting said X-rays, said detector means being made of a material which may deteriorate on exposure to said X-rays, means for moving an object under study between said source and said detector means so that a shadow of said object falls on said detector means, blinder means having a gap through which said X-rays must pass in order to fall on said detector means, and means for moving said blinder means in synchronism with the movement of said object under study so that said gap is over said detector means substantially only when an X-ray shadow of said object falls on said detector means
wherein said blinder means has at least one recess formed in an edge thereof, sensor means at a location within said recess which is so shielded from X-rays that said sensor means is protected by the material of said blinder means against radiation damage by X-rays from said source, and mirror means positioned on said blinder means for reflecting non-X-ray signals onto said sensor means in said recess for indicating to said sensor means the physical position of said blinder means relative to the boundary of a field of said X-rays.

6. The scanner of claim 5 further comprising a source of said non-X-ray signals, the distribution of said non-X-ray signals from said source being substantially the same as the distribution of said X-rays so that the presence or absence of said non-X-ray signals corresponds to the presence or absence of said X-rays so that said non-X-ray signals falling upon said sensor means indicating that said sensor means is in the presence of X-rays.

7. The scanner of claim 6 further comprising servo means for controlling the movement of said blinder means, and control means comprising a closed loop for operating said servo means, said loop comprising said sensor means, a central processor, and motors for driving said blinder means to position said sensor means.

8. The scanner of claim 7 wherein said source of non-X-ray signals includes a laser means, and said sensor means includes a photocell which is sensitive to the output of said laser means, differential amplifier means having a first input energized at a reference level and a second input energized by an output of said photocell, and means responsive to an output of said amplifier for operating said central processor.

9. A process for dynamically scanning a moving object, said process comprising the steps of:
(a) providing a detector means in a fan-shaped field of X-rays, said detector means being receptive to X-rays over a substantial angular part of said fan-shaped field;
(b) moving said object through said field in a manner which casts a shadow of said object upon a portion of said detector means during a predetermined part of the movement;
(c) moving a blinder means which is made of a material that is opaque to X-rays in synchronism with the movement of the shadow of said object, said blinder means normally shielding said detector means from said X-rays, said blinder means having a gap to admit passage of said X-rays through said blinder means; and
(d) positioning said gap to enable said X-rays to fall on substantially only that portion of said detector means where a shadow of said object is actually being cast upon said detector means.

10. The process of claim 9 wherein said blinder means comprises two independently movable, horizontally aligned plates defining said a gap between them, further comprising the step of independently adjusting the positions of said two plates relative to each other in order to select a width for said gap.

11. The process of claim 9 further comprising the steps of using light for simulating the distribution and boundary of said X-ray field, and detecting the presence of said X-ray field by means of a light-responsive sensor without exposing said sensor to said X-rays.

12. The process of claim 11 further comprising the step of shielding said light-responsive sensor from said X-rays while exposing it to said light.

13. The process of claim 12 further comprising the step of disposing said light-responsive sensor in a recess formed within the blinder means so that said material which is opaque to X-rays protects said light-responsive sensor from said X-rays.

14. The process of claim 13 further comprising the step of reflecting said light into said recess by means of an x-ray transparent mirror so that said light but not said X-rays fall upon said light-responsive sensor.

15. A dynamic X-ray machine comprising a frame supporting a source of X-rays and a detector means for mutual movement over two spaced parallel planes such that a field of said X-rays may be directed toward said detector means from any of many different positions, said frame enabling said two planes to move toward or away from each other, means associated with said frame for transporting an object along a path between said spaced parallel planes, said path casting a shadow of said object in the field of X-rays directed toward a said detector means, a pair of blinder plates which are separated from each other by a gap and which are mounted to travel adjacent said path for shielding said detector means from said X-rays, means for synchronizing the transportation of said object and the movement of said blinder plates to position said gap over said detector means at a time when the shadow of said object is being cast in the X-ray field falling on said detector means, sensor means mounted on said blinder plates for indicating the position of said gap throughout said travel, and means for controlling said synchronous transport of said object and the movement of said blinder plates.

16. The machine of claim 15 further comprising means responsive to the output of said detector means for assembling an image of said object responsive to said shadow scanning across the detector means.

17. The machine of claim 16 further comprising means for adjusting the width of said gap by moving said blinder plates toward or away from each other.

* * * * *